(12) United States Patent
Yuen et al.

(10) Patent No.: US 9,241,513 B2
(45) Date of Patent: Jan. 26, 2016

(54) ITEM OF CLOTHING FOR DAILY PHARMACOLOGICAL TREATMENT OF A FUNGAL INFECTION

(75) Inventors: Marcus Chun Wah Yuen, Hong Kong (HK); Joanne Yiu Wan Yip, Hong Kong (HK); Kevin Cheuk, Hong Kong (HK); Chi Wai Kan, Hong Kong (HK); Shuk Yan Cheng, Hong Kong (HK)

(73) Assignee: The Hong Kong Polytechnic University, Hong Kong (HK)

( * ) Notice: Subject to any disclaimer, the term of this patent is extended or adjusted under 35 U.S.C. 154(b) by 335 days.

(21) Appl. No.: 13/219,248

(22) Filed: Aug. 26, 2011

(65) Prior Publication Data
US 2013/0052248 A1 Feb. 28, 2013

(51) Int. Cl.
| | |
|---|---|
| *A41B 11/00* | (2006.01) |
| *D06M 23/12* | (2006.01) |
| *D06M 23/16* | (2006.01) |
| *D06M 23/00* | (2006.01) |
| *D06M 23/08* | (2006.01) |
| *A43B 1/04* | (2006.01) |
| *A61K 35/66* | (2015.01) |
| *A61M 35/00* | (2006.01) |
| *D06M 16/00* | (2006.01) |

(52) U.S. Cl.
CPC ............... *A41B 11/00* (2013.01); *A61M 35/00* (2013.01); *D06M 16/00* (2013.01); *D06M 23/12* (2013.01); *A41B 2400/34* (2013.01); *A41B 2400/60* (2013.01)

(58) Field of Classification Search
CPC ... A41B 11/00; A41B 2400/60; A61M 35/00; D06M 16/00; D06M 23/12; A61K 35/66
See application file for complete search history.

(56) References Cited

U.S. PATENT DOCUMENTS

| | | | |
|---|---|---|---|
| 4,195,364 A | 4/1980 | Bengtsson et al. | |
| 4,561,267 A * | 12/1985 | Wilkinson et al. | 66/178 A |
| 4,625,336 A | 12/1986 | Derderian | |
| 6,354,114 B1 | 3/2002 | Sghiatti | |
| 6,401,250 B1 | 6/2002 | McNabb | |
| 6,442,760 B2 | 9/2002 | Moretti | |
| 6,817,030 B2 | 11/2004 | Desai | |
| 7,069,600 B1 * | 7/2006 | Romay | 2/239 |
| 7,198,800 B1 * | 4/2007 | Ko | 424/443 |
| 7,669,250 B2 | 3/2010 | Baron et al. | |
| 7,670,968 B2 | 3/2010 | Bohringer et al. | |
| 7,759,274 B1 | 7/2010 | Bohringer | |
| 7,833,960 B2 | 11/2010 | Lei et al. | |
| 7,838,037 B2 | 11/2010 | Kvitnitsky et al. | |
| 2003/0099666 A1 * | 5/2003 | Battaglia | 424/195.18 |
| 2004/0209954 A1 * | 10/2004 | Lukacsko | 514/554 |
| 2005/0273903 A1 | 12/2005 | Rudman | |
| 2012/0284902 A1 * | 11/2012 | Matsuo et al. | 2/239 |

FOREIGN PATENT DOCUMENTS

| | | | |
|---|---|---|---|
| AU | 2008201219 A1 * | 10/2008 | |
| JP | 01121241 A * | 5/1989 | |
| JP | 2010106397 A * | 5/2010 | |
| WO | WO 2007070094 A2 * | 6/2007 | |

* cited by examiner

*Primary Examiner* — Michael G Hartley
*Assistant Examiner* — Nabila Ebrahim
(74) *Attorney, Agent, or Firm* — Muncy, Geissler, Olds & Lowe, P.C.

(57) ABSTRACT

An item of clothing (10) for daily pharmacological treatment of a fungal infection, comprising: a textile material (20) to manage moisture when the item of clothing (10) is worn; microcapsules (30) grafted on the textile material (20); and antifungal agents encapsulated within the microcapsules (30) to pharmacologically treat the fungal infection when released from the microcapsules (30).

24 Claims, 13 Drawing Sheets

ITEM OF CLOTHING FOR DAILY PHARMACOLOGICAL TREATMENT OF A FUNGAL INFECTION

TECHNICAL FIELD

The invention concerns an item of clothing for daily pharmacological treatment of a fungal infection. Also, the invention concerns a method of manufacturing the item of clothing. Further, the invention concerns a method and system for daily pharmacological treatment of a fungal infection.

BACKGROUND OF THE INVENTION

Fungi cause a wide spectrum of diseases. The most common examples are localized infections of the skin and mucous membranes, such as tinea pedis, vaginal yeast infections and infections of keratinized nails. Tinea pedis, also known as athlete's foot, is a form of ringworm associated with highly contagious yeast-fungi colonies. Tinea pedis is estimated to be the second most common skin disease in the United States behind acne, and up to 15% of the population may manifest the disease. Based on a review, tinea pedis may be present in a particular patient as one of the several syndromes. Typically, three variants are seen as shown in the following:

a) Interdigital type of tinea pedis.
  This is the most common form usually manifested in the interspace of the fourth and fifth digits, and may spread to the underside of the toes. Patients often complain of itching and burning sensations on the feet accompanied by malodor.
b) Moccasin type tinea pedis
  This type is a more severe, prolonged form of tinea pedis that covers the bottom and lateral aspects of the foot. Its appearance is in the form of a slipper or moccasin. The skin of the inflamed area in this type of infection is often scaly and hyperkeratotic with erythema around the soles and sides of the foot.
c) Vesiculobullous type of tinea pedis
  This type comprises pustules or vesicles on the instep and adjacent plantar surfaces of the feet, and is less common.

Both non-pharmacological and pharmacological treatments are applied to treat tinea pedis. Non-pharmacological treatment focuses on educating patients about the predisposing factors, and the chronic nature of the disease. The patients should try to eliminate the moisture that provides the environment for infection.

Keeping the feet clean and dry with the toenails trimmed reduces the incidence of skin disease on the feet. Wearing open-toed shoes and avoiding skin maceration are also recommended. However, some patients may not be able to wear the open-toed shoes due to reasons of etiquette, safety, or work requirements. In the market, there are some hygienic products such as anti-bacteria or anti-odor socks for common use. Silver ions or ceramic magnetic powders are used to eliminate bacteria resulting in controlling the odor-causing bacteria and preventing bad odor. However, for tinea pedis patients, these products are not suitable due to the lack of pharmacological treatment.

Pharmacological treatments involve the use of topical antifungal agents such as ketoconazole, terbinafine, econazole, or cicloprox creams. The treatments are applied onto the normal skin about 2 cm beyond the affected area. For example, 1% terbinafine cream is applied twice a day for one week. However, the data have shown that this kind of treatment fails to cure about one-third of patients with tinea pedis. Most of the relapses are due to poor compliance as the topical treatment should continue a minimum of one more week after the symptoms have cleared up.

In order to increase the successful rate of curing patients with tinea pedis and reduce the chances of relapse, there is a strong need to design and develop a convenient pharmacological treatment and protective measure which will reduce the suffering of disease symptoms.

SUMMARY OF THE INVENTION

In a first preferred aspect, there is provided an item of clothing for daily pharmacological treatment of a fungal infection, comprising:
  a textile material to manage moisture when the item of clothing is worn;
  microcapsules grafted on the textile material; and
  antifungal agents encapsulated within the microcapsules to pharmacologically treat the fungal infection when released from the microcapsules.

The textile material may be any one from the group consisting of: cotton, polyester, polyvinyl chloride (PVC), keratin fibers, wool, Spandex™, Tencel, acrylic, bamboo fiber, flax, lyocell, rayon, cellulosic acetates and COOLMAX™.

A wall shell for the microcapsules may be any one from the group consisting of: chitosan and gelatin.

The fungal infection may be any one from the group consisting of: interdigital tinea pedis, moccasin tinea pedis and vesiculobullous tinea pedis.

The item of clothing may be a sock.

The sock may be in the form of a toe sock and has a knitting structure in the form of a single jersey and is knitted as a moss stitch, the sock having at least one ribbed portion to tightly secure the sock to the foot.

The item of clothing may further comprise an anti-bacterial material contained in the textile material, the anti-bacterial material being any one from the group consisting of: ceramic magnetic powder, silver-ion, zinc-ion, potassium-ion copper-oxide, calcium-ion, titanium-dioxide, triclosan, chloroxylenol, chitosan and quaternary ammonium compounds.

The antifungal agents may be released at a predetermined rate to ensure stability and control.

The antifungal agents may be oil-soluble or water-soluble.

The oil-soluble agents may include any one from the group consisting of: ketoconazole, clotrimazole, miconazole nitrate, sertaconazole nitrate, griseofvlin and tolnaftate.

The water-soluble agents may include any one from the group consisting of: a salt form of amorolfine, ciclopi rox. butenafine, imidazole and terbinafine.

The item of clothing may be worn only once for twelve hours for pharmacological treatment and as an anti-bacterial and/or antifungal socks for further daily use.

The microcapsules may be produced with the chitosan wall shell by coacervation.

The microcapsules may be produced with the gelatin wall shell by emulsion hardening.

The microcapsules may be grafted on the textile material by any one from the group consisting of: padding, exhaustion, spraying and printing.

The microcapsules may be grafted on the textile material by a surface modification method and thermal fixation.

The surface modification method may be atmospheric pressure plasma (APP) treatment.

In a second aspect, there is provided a method for daily pharmacological treatment of a fungal infection, the method comprising:

wearing an item of clothing made from a textile material to manage moisture, the textile material having microcapsules grafted thereon, and antifungal agents are encapsulated within the microcapsules;

wherein the antifungal agents are released from the microcapsules to pharmacologically treat the fungal infection when the item of clothing is worn.

In a third aspect, there is provided a system for pharmacological treatment a disease or infection, the system comprising:

an item of clothing made from a textile material;
microcapsules grafted on the textile material; and
agents encapsulated within the microcapsules to pharmacological treat the disease or infection when released from the microcapsules;
wherein the microcapsules are grafted on the textile material by a surface modification method and thermal fixation.

In a fourth aspect, there is provided a method for manufacturing an item of clothing for daily pharmacological treatment of a fungal infection, the method comprising:

knitting a textile material to form an item of clothing such that moisture is managed when the item of clothing is worn;
grafting microcapsules on the textile material; and
encapsulating antifungal agents within the microcapsules to pharmacologically treat the fungal infection when released from the microcapsules.

The present invention provides a pair of hygienic socks to combine a convenient pharmacological treatment by using microencapsulation processing and moisture management to reduce microbial overgrowth, thereby reducing the effects of the disease on their quality of life.

Applying both non-pharmacological and pharmacological treatments can cure patients with tinea pedis. In addition, corrective measures on the personal hygiene can also reduce relapses. However, many patients neglect their foot health and never seek medical advice, resulting in the prevalence of foot disease.

In order to increase the success rate of curing patients with tinea pedis and reduce the chances of a relapse, a convenient pharmacological treatment and protective measure which will reduce the suffering of disease symptoms is provided. There are different designs of the sock that can accommodate three variants of tinea pedis including interdigital, moccasin, and vesiculobullous. The sock allows dermatologists to apply different topical antifungal agents inside the microcapsules which will be continuously released onto the infected skin of patients in a controlled manner.

BRIEF DESCRIPTION OF THE DRAWINGS

An example of the invention will now be described with reference to the accompanying drawings, in which.

DETAILED DESCRIPTION OF THE DRAWINGS

Figure 1:
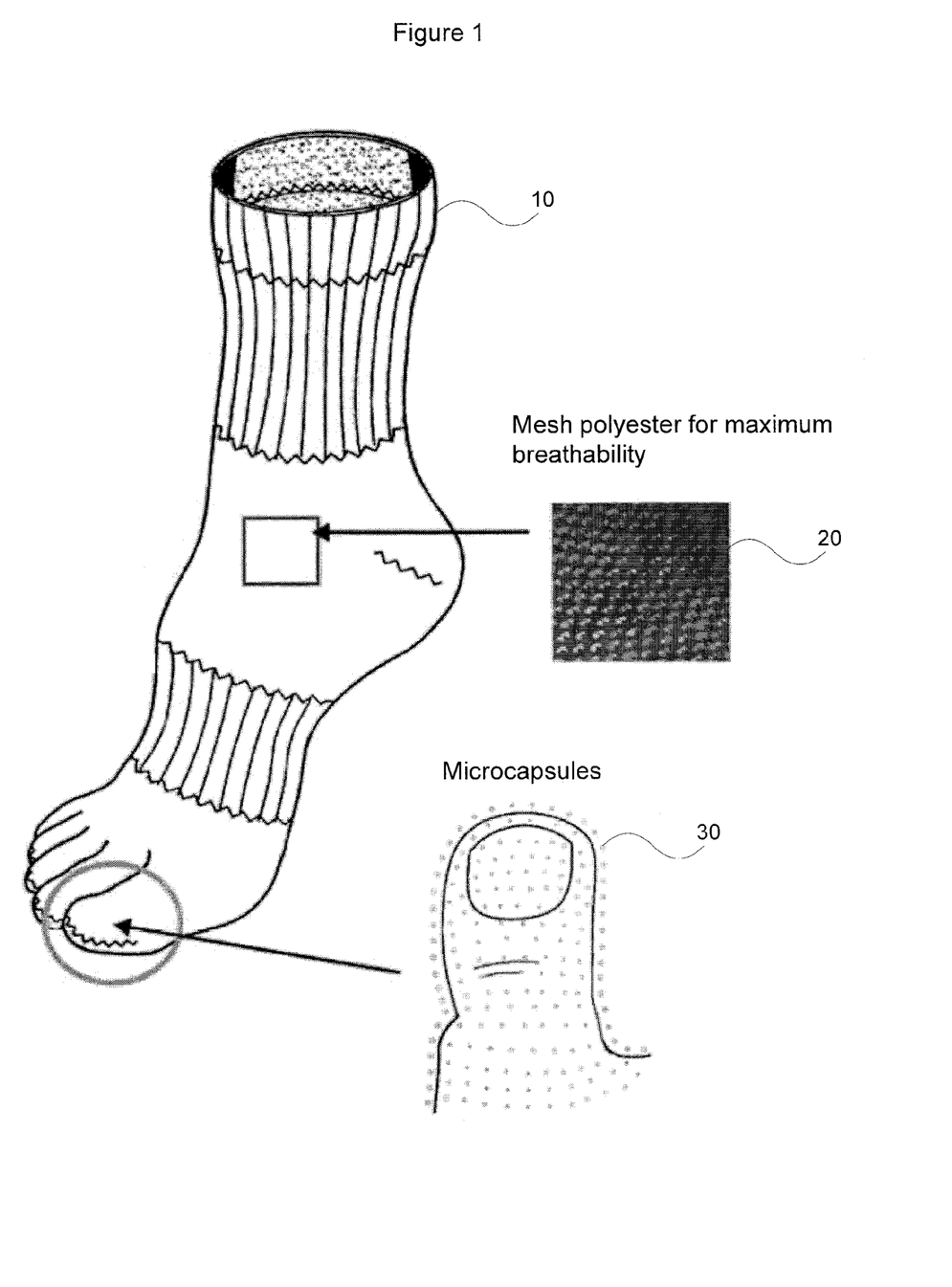
FIG. 1 is a schematic diagram of an item of clothing for daily pharmacological treatment of a fungal infection in accordance with an embodiment of the present invention.

Referring to FIG. 1, an item of clothing for daily pharmacological treatment of a fungal infection is provided. The item of clothing is preferably a hygienic sock 10. The sock 10 comprises a textile material 20 to manage moisture when the item of clothing is worn. The sock 10 comprises microcapsules 30 to pharmacological treat the fungal infection. The microcapsules 30 are grafted on the textile material 20. Active antifungal agents are encapsulated within the microcapsules 30.

Moisture Management

The textile material 20 may be: cotton, polyester, polyvinyl chloride (PVC), keratin fibers, wool, Spandex™, Tencel, acrylic, bamboo fibre, flax, lyocell, rayon, cellulosic acetates and COOLMAX™. Cellulosic fibers and synthetic fibers are suitable materials for the sock 10. Anti-bacterial materials such as ceramic magnetic powder, silver-ion, zinc-ion, potassium-ion copper-oxide, calcium-ion, titanium-dioxide, triclosan, chloroxylenol, chitosan or quaternary ammonium compounds may also be incorporated with the textile material 20 for reducing bad odor and eliminating bacteria. The textile material 20 may be woven or knitted to form the sock 10 to ensure good breathability. One construction design for the sock 10 is a toe sock. In a toe sock, each individual toe is individually encased by the text material 20, and this would increase contact surface area for the microcapsules 30 and the skin of the foot. These features provide good moisture management which is an important element for successfully treating the fungal infection. Moisture management of socks is different from that of sportswear or active wear as the environment is occlusive. Moisture management reduces microbial overgrowth for patients.

Microcapsules

Microencapsulation is a micropackaging technique that involves the production of microcapsules which act as barrier walls of solids or liquids inside. The microcapsules are produced by depositing a thin polymer coating on the small solid particles or liquid droplets, or dispersions of solids in liquids. The core contents of the microcapsules are released under controlled conditions to suit a specific purpose. The release mechanisms of the core contents vary depending on the selection of wall materials, but more importantly, the specific end uses. The core content may be released by friction, pressure, change of temperature, diffusion through the polymer wall, dissolution of the polymer wall coating or biodegradation.

An advantage of using microencapsulation technology is its ability to protect active ingredients from the external environment, i.e. heat, acidity, alkalinity, moisture or evaporation. In other words, the antifungal agents can be stored in the microcapsules and released onto the skin during daily wear. Another advantage is its controlled release properties which seem to be the best choice for increasing efficiency.

Both non-pharmacological and pharmacological treatments as aforementioned can cure patients with tinea pedis. In addition corrective measures for personal hygiene can also reduce relapses. However, many patients neglect their foot health and never seek medical advice, resulting in the prevalence of foot disease. The socks provide a convenient pharmacological treatment and good moisture management which can reduce the microbial overgrowth for patients with tinea pedis, thereby reducing the effects of the disease on the quality of life.

A microencapsulation technique is used to encapsulate various types of antifungal agents. Microencapsulation techniques can be generally classified into two groupings: physical and chemical processes. Physical processes include spray drying, centrifugal extrusion, air suspension coating, and pan coating. Chemical processes include: complex coacervation, polymer-polymer incompatibility, interfacial polymerization, and in situ polymerization.

A coacervation technique or emulsion hardening technique is used to produce microcapsules with a stable and controlled release. Selection of suitable wall shells and core materials is an important factor for consideration during the development of novel microencapsulation systems. Careful selection of wall shells is essential as the materials should be biologically safe to the human body. Preferably, chitosan or gelatin (which is a biocompatible polymer), is used to produce the wall shell of the microcapsules. Core materials in the form of oil-soluble (for example, ketoconazole, clotrimazole, miconazole nitrate, sertaconazole nitrate, griseofvlin or tolnaftate) or water-soluble (for example, a salt form of amorolfine, ciclopirox. butenafine, imidazole or terbinafine) antifungal agents are encapsulated by the chitosan or gelatin wall material to form a secure protection from the external environment. Synthesis of chitosan or gelatin microcapsules which contain antifungal agents are based on coacervation or emulsion hardening techniques due to their low cost efficiency and ease of application.

Chitosan is non-toxic, biodegradable and biocompatible, and has been used as a biopolymer or a crude material. The techniques to encapsulate chemicals with chitosan include ionotropic gelation, spray drying, emulsion phase separation, coacervation, chitosan coatings or polymerization of a vinyl monomer in the presence of chitosan. Furthermore, chitosan also shows a good anti-bacterial activity against various bacteria and fungi because of its polycationic nature. Chitosan can stop the growth of a number of gram-positive and gram-negative bacteria by inhibiting the normal metabolism of microorganisms through the ionic interaction at cell surfaces and eventually killing the cell.

Figure 2:
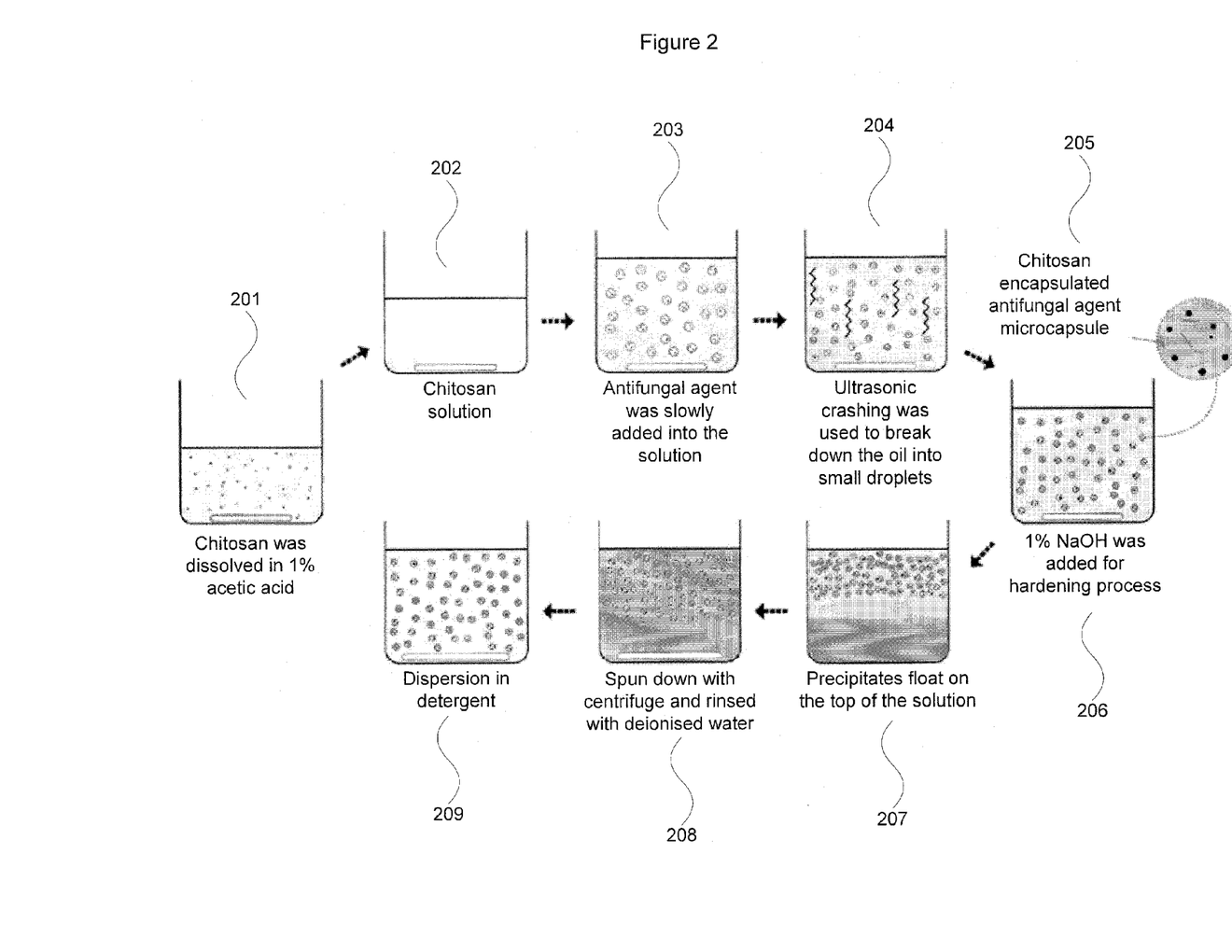
FIG. 2 is a process flow diagram of developing an oil-in-water (O/W) microencapsulation system using chitosan nature biopolymer in accordance with an embodiment of the present invention.

Turning to FIG. 2, the process of developing oil-in-water (O/W) microencapsulation systems using chitosan nature biopolymer is depicted. The microencapsulation process for an oil-in-water (O/W) microencapsulation system involves dissolving chitosan in 1% acetic acid. Next, the chitosan solution 202 which contains acetic or formic acid is blown into a precipitating medium, such as aqueous or methanolic sodium hydroxide (NaOH). Oil-soluble antifungal agents 203 are intermixed together with the chitosan solution by using a magnetic stir plate at a high stirring speed to provide an oil-in-water (O/W) emulsion. Ultrasonic crashing 204 is used to break down the oil into small droplets. The chitosan encapsulated antifungal agent microcapsules 30 are formed 205. 1% of aqueous or methanolic NaOH is added for hardening 206 the microcapsules 30. The precipitates float 207 on top of the solution. The solution is spun down 208 using a centrifuge and rinsed with deionized water. The precipitates formed are dispersed 209 by using different nonionic surfactants to prevent agglomeration of the microcapsules 30. The maintenance of even particle size distribution of microcapsules is important.

The microencapsulation process for a water-in-oil (W/O) microencapsulation system requires gelatin and water-soluble antifungal agents to be dissolved in deionized water at a temperature of 40 to 60° C. for few minutes. Next, the solution is poured into 100% pure canola oil to form a water-in-oil (W/O) emulsion with the aid of a Span 80 surface-active agent. The mixture is intermixed for few minutes by using a magnetic stir plate at a very high speed to form a stable W/O emulsion. The emulsion is then further mixed by using an ultrasonic processor for a few minutes to break down the emulsion into smaller droplets. The W/O emulsion is continually stirred while formaldehyde is added to crosslink the microcapsules for a few hours at room temperature. The addition of formaldehyde is as slow as possible in order to maintain the system stability. Afterwards, the precipitation process is conducted by adding acetone into the solution. The addition of acetone is also aimed at microcapsule separation and dehydration. The precipitates, which are the gelatin microcapsules that contain an antifungal agent, are filtered, and then dried at room temperature.

Oil-in-water (O/W) microencapsulation system or water-in-oil (W/O) microencapsulation system is the medium during the microencapsulation processes. For example, if the antifungal agent is oil-soluble, then the microencapsulation process is carried out in a water medium and therefore oil-in-water (O/W) microencapsulation system is used. The benefits of the system are largely dependent on the choice of wall materials, for example, chitosan or gelatin. This is because different wall materials may require different techniques to synthesize.

If the wall material is chitosan, the microencapsulation technology used is coacervation. Chitosan is suitable for encapsulating hydrophobic core materials, it has a short synthesis time and is cost effective. However, the release of core materials requires friction and microcapsules are stored in a wet condition.

If the wall material is gelatin, the microencapsulation technology is emulsion hardening. Gelatin is suitable for encapsulating hydrophilic core materials. The release of core materials is by means of simple diffusion through moisture. It is cost effective and is stored in a dry condition which makes it easier for storage. However, there is a long synthesis time and a low dose of formaldehyde is used.

Referring to FIGS. 4 to 9, scanning electron microscopy (SEM) is used to demonstrate the surface morphologies of different microcapsules. Fourier transform infrared spectroscopy (FTIR), x-ray diffraction (XRD) and x-ray photoelectron spectroscopy (XPS) are used to evaluate and identify the microcapsule products. Differential scanning calorimetry (DSC) will be used to study the thermal properties of the microcapsules. A particle size analyser and UV-vis spectrometer will be employed to determine the particle size distribution of microcapsules and their controlled-release properties under different conditions.

There are several fabrication techniques suitable for preparing the sock 10 covered with the microcapsules 30. The techniques include: padding, exhaustion, spraying and printing. For padding, the fabric (textile material 20) is immersed into the microcapsule solution and further padded by a padder at a constant speed and pressure followed by curing process for fixation. Padding is simple and only a low temperature is required. However, pressure may break the microcapsules 30. Therefore, it is desirable for the microcapsules 30 to be grafted onto the textile fabric 20 without bursting during the padding process. For exhaustion, the fabric 20 is immersed into the microcapsule solution and soaked for a pre-determined duration at an elevated temperature. The fabric is then extracted from the solution followed by curing for fixation. No pressure is required and therefore the breakage of microcapsules 30 is minimized. However, a high temperature is required. For spraying, the microcapsules 30 are sprayed onto the fabric 20 at a constant pressure to achieve even distribution on the fabric. Spraying is simple, requires a low temperature and no pressure. However, there may be uneven distribution of the microcapsules 30 on the fabric 20. For printing, a print paste is prepared by mixing both the microcapsules 30 and the appropriate binders together with a thickener. The print paste is then printed onto the fabric 20 samples using a screen frame. Printing is simple and a low temperature is required. However, there is poor hand feel.

In one embodiment, the chitosan or gelatin microcapsules 30 are embedded in textiles by a new fabrication technique which consists of both pre-treatment processes and post-treatment processes. Surface modification methods, for example, atmospheric pressure plasma (APP) treatment, serving as the pre-treatment processes enhance the adhesion between microcapsules 30 and surface of the fabric 20. An APP jet is used for treating the textile materials 20 as it can generate uniform reactive gases which can also be applied to the surface of any shaped objects. The chitosan or gelatin microcapsules 30 are then grafted on the plasma pre-treated textiles materials 20 using different fabrication techniques including padding process, exhaustion process, spraying process and printing methods as described above. Thermal fixation is used for the post-treatment processes. During the thermal fixation, the thermal set agents are cured at 130° C. to 170° C. for a few minutes. Monomers or oligomers, with or without a crosslinker in the fixing agents can trigger a reaction of the species with the fibers as well as the formation of a polymeric film on the fibers. Through a chemical linkage or via entrapment in the film, the microcapsules 30 are held onto the substrate. However, the thermal treatment can give contradictory effects on washing durability of microcapsules 30. Higher temperature and longer curing time usually increase the fastness of microcapsules 30 on textiles 20, with decreased drugs inside the microcapsules. The higher the temperature in curing, the more the loss of drug will be. Consequently, a suitable binder or cross-linker is selected to avoid breakage of microcapsules 30 during the application. For example, UV curing will be a medium for a quick and low temperature process that avoids the breakage of microcapsules 30 and evaporation of the core component which frequently occur in thermal curing, thereby enhancing the performance durability. The processing parameters including curing time, temperature or UV intensity are optimized to enhance manufacturing yield.

Antifungal Agents

Various types of antifungal agents may be encapsulated for the pharmacological treatment of athlete's foot. Two different types of antifungal agents may be used. One type of antifungal agent is in oil-soluble form such as ketoconazole, clotrimazole, miconazole nitrate, sertaconazole nitrate, griseofvlin or tolnaftate. The other type of antifungal agent is water-soluble such as a salt form of amorolfine, ciclopi rox. butenafine, imidazole or terbinafine. These two types of antifungal agents are encapsulated by the chitosan or gelatin wall material to form a secure protection from the external environment.

Figure 3:
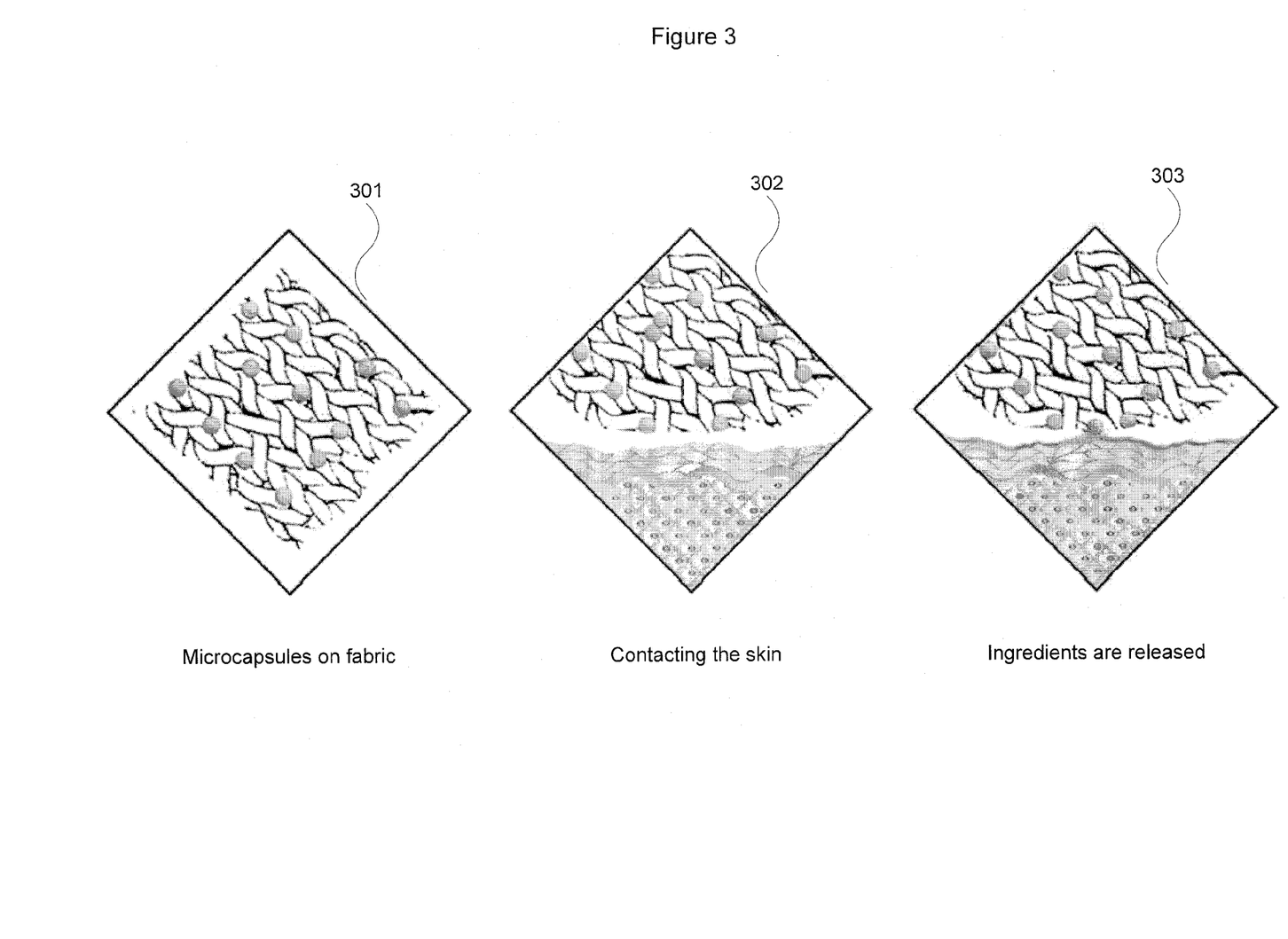
FIG. 3 is a process flow diagram of antifungal agent releasing/diffusion mechanism of the item of clothing of FIG. 1.
Figure 4:
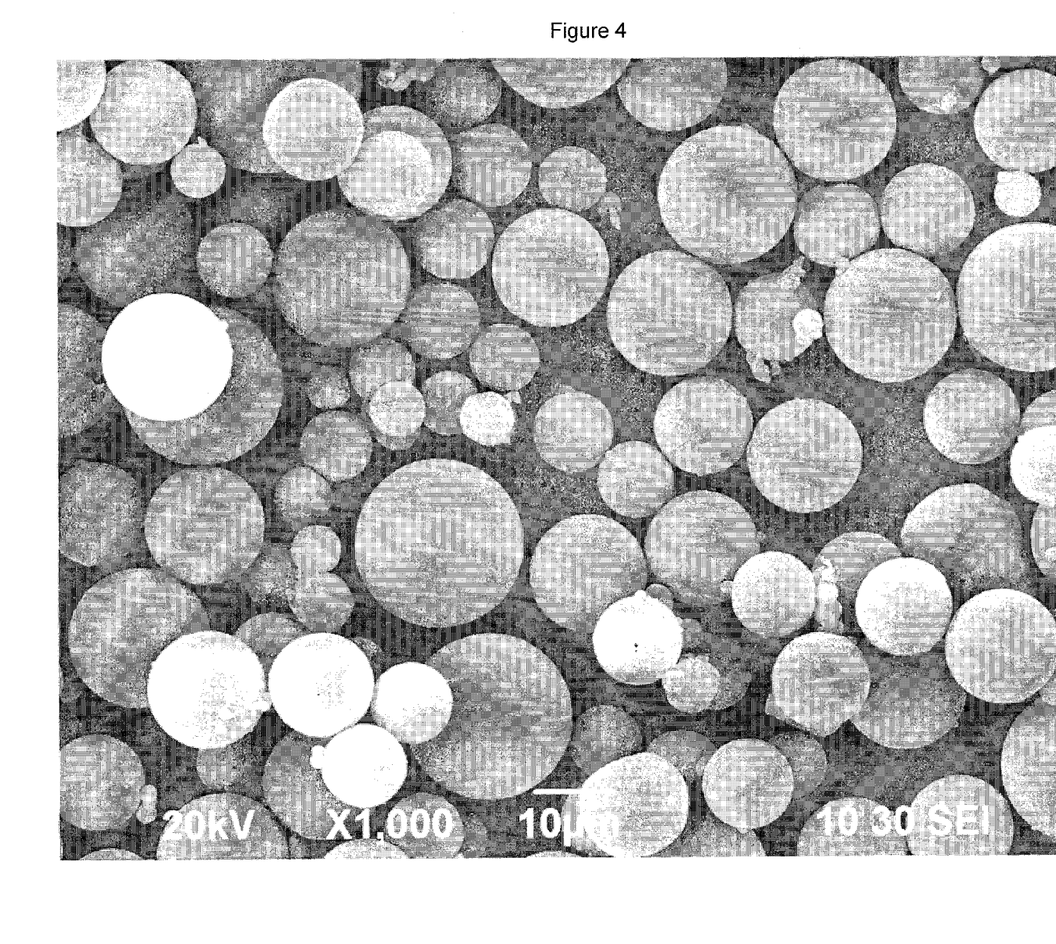
FIG. 4 is a SEM Image of Terbinafine Hydrochloride-loaded Microcapsules at 1000× magnification.
Figure 5:
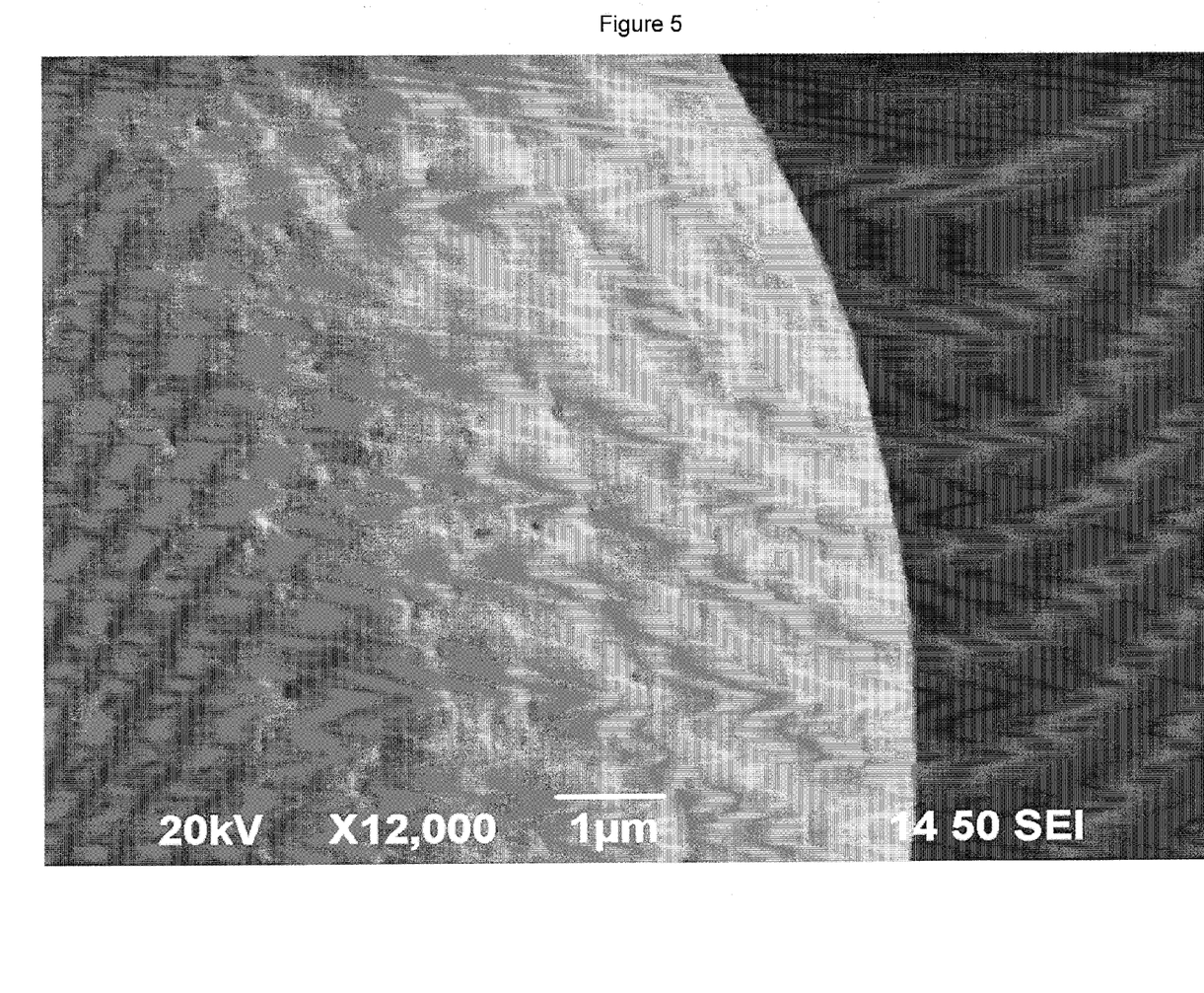
FIG. 5 is a SEM Image of Terbinafine Hydrochloride-loaded Microcapsules at 12000× magnification.
Figure 6:
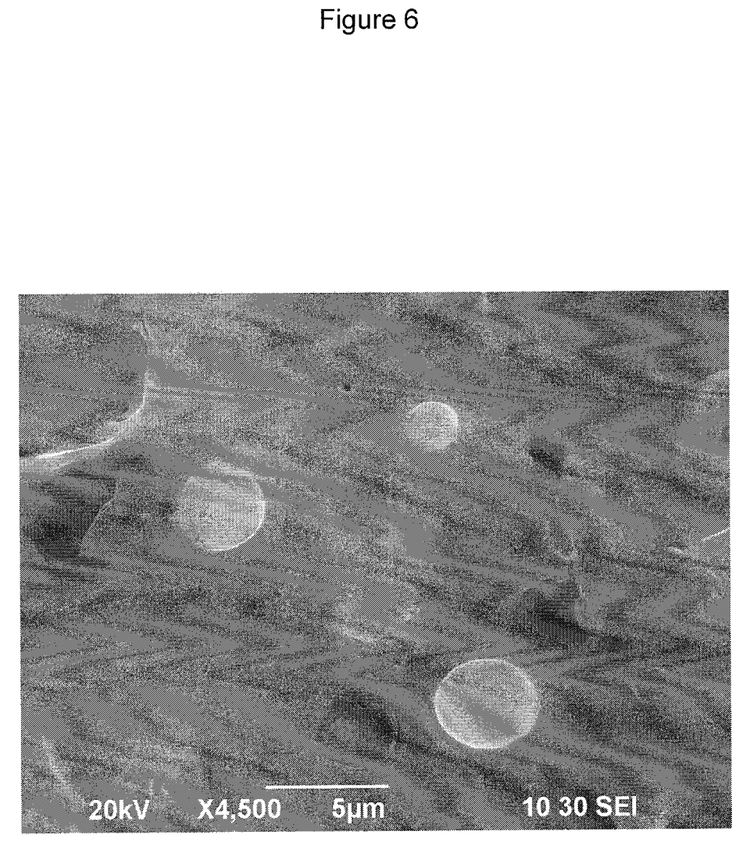
FIG. 6 is a SEM Image of Chitosan/Miconazole Nitrate Salt-loaded Microcapsules as Control.
Figure 7:
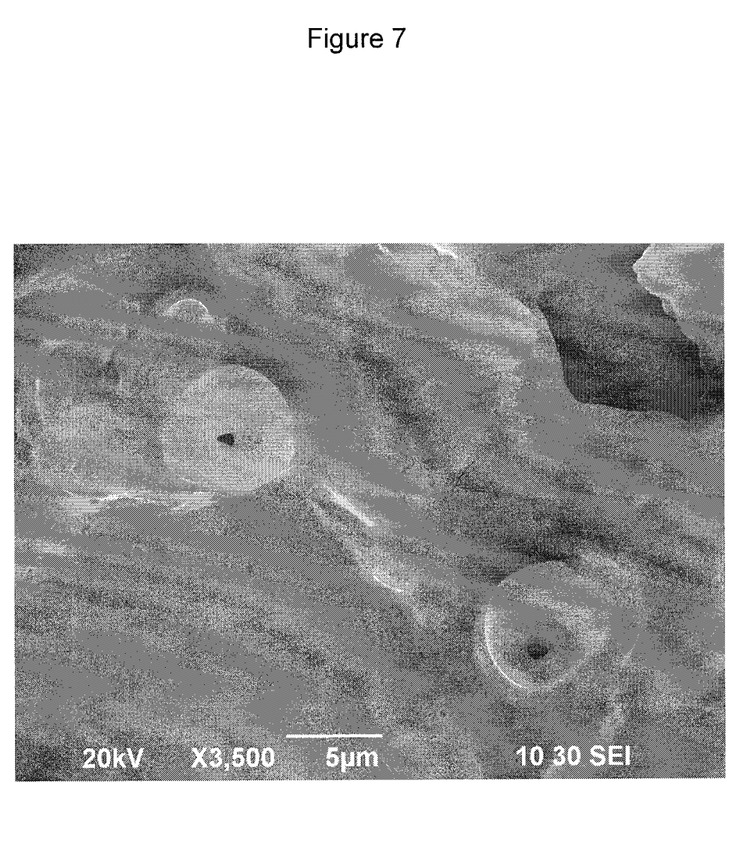
FIG. 7 is a SEM Image of Chitosan/Miconazole Nitrate Salt-loaded Microcapsules after stirring.
Figure 8:
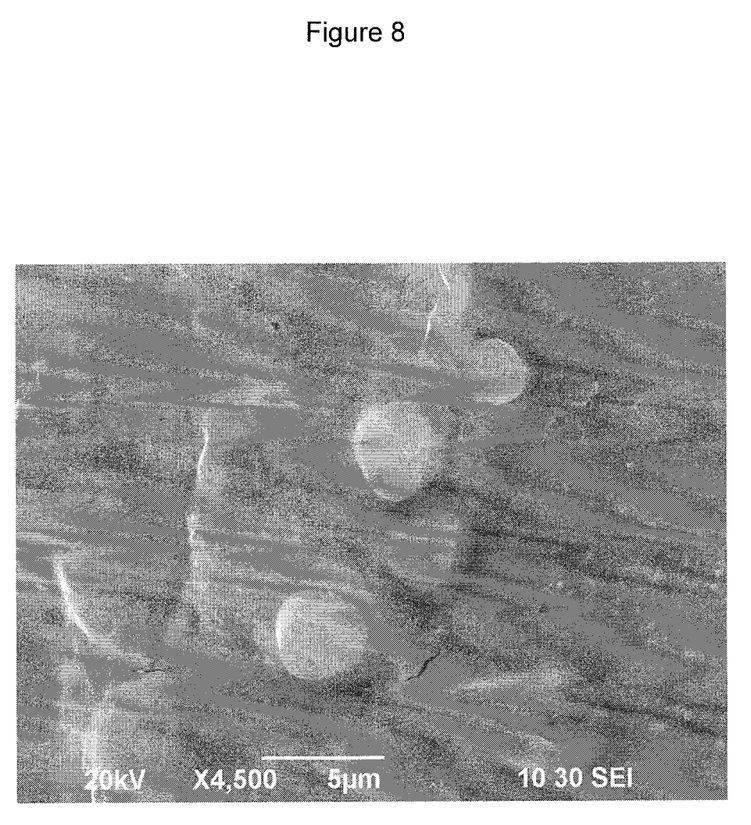
FIG. 8 is a SEM Image of Chitosan/Clotrimazole-loaded Microcapsules as Control.
Figure 9:
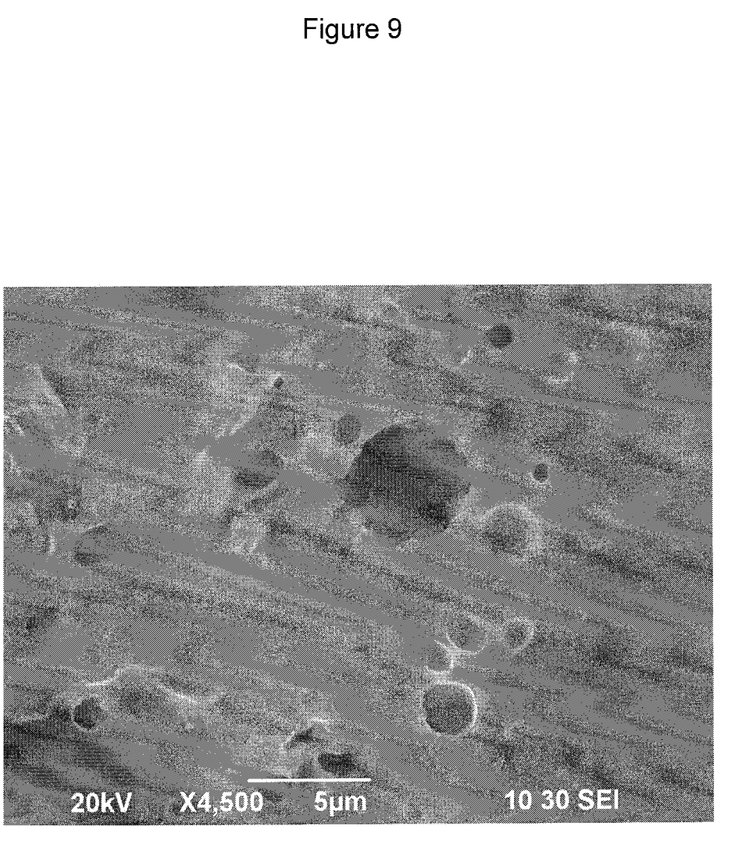
FIG. 9 is a SEM Image of Chitosan/Clotrimazole-loaded Microcapsules after stirring.

The rate of release of the active antifungal agents liberated from the microcapsules 30 of the textile material 20 is controlled to maintain the efficiency of the pharmacological treatment. The release mechanism of the core contents/active antifungal agents varies depending on the selection of wall materials for the microcapsules 30 and more importantly, its specific end use. The core content/active antifungal agent may be released by friction, pressure, change of temperature, diffusion through the polymer wall, dissolution of the polymer wall coating or by biodegradation. Preferably, chitosan or gelatin are used as wall materials for the microcapsule 30. Therefore, the release mechanisms are by mean of simple diffusion through moisture or by friction. On contact with the skin, the socks 10 are designed to transfer/release the active antifungal agent for pharmacological treatment of the fungal infection. Turning to FIG. 3, the process of antifungal agent releasing/diffusion mechanism of the socks 10 is depicted. The microcapsules 30 are grafted on and present in the textile fabric 20. When the sock 10 is worn by a patient there is contact 302 between the textile fabric 20 and the skin of the foot. The contact between the textile fabric 20 and the skin causes the antifungal agents to be released 303 either by friction between the skin and textile fabric 20 or moisture from the skin.

The socks 10 are designed to release the active antifungal agent for pharmacological treatment in a controlled manner. The active antifungal agents can be absorbed slowly by the patient's skin, instead of absorbing once at contact. Under a slow-release delivery mechanism, the active antifungal agents can be released to human skin in a controlled way in order to avoid overdose. To control the release of microcapsules, possible adjustment can be conducted during the synthesis processes. For example, increasing the concentration of chitosan can make the chitosan wall become thicker thereby lowering the release rate. For the gelatin microcapsules, adjusting the crosslinking time during the synthesis processes is one of the ways to control the release rate of the active antifungal agents. When the microcapsules 30 are releasing the ingredients, they are not expected to stop or else it may affect the efficiency of treatment towards the patients.

The socks 10 are for a single use application since most or all the microcapsules 30 would not be usable after washing. One reason for selecting single use rather than re-current use of the same sock 10 is to ensure that sufficient antifungal agent-loaded microcapsules 30 are released to the patient every day. Patients are instructed to wear the socks 10 daily for at least twelve hours.

Figure 10:
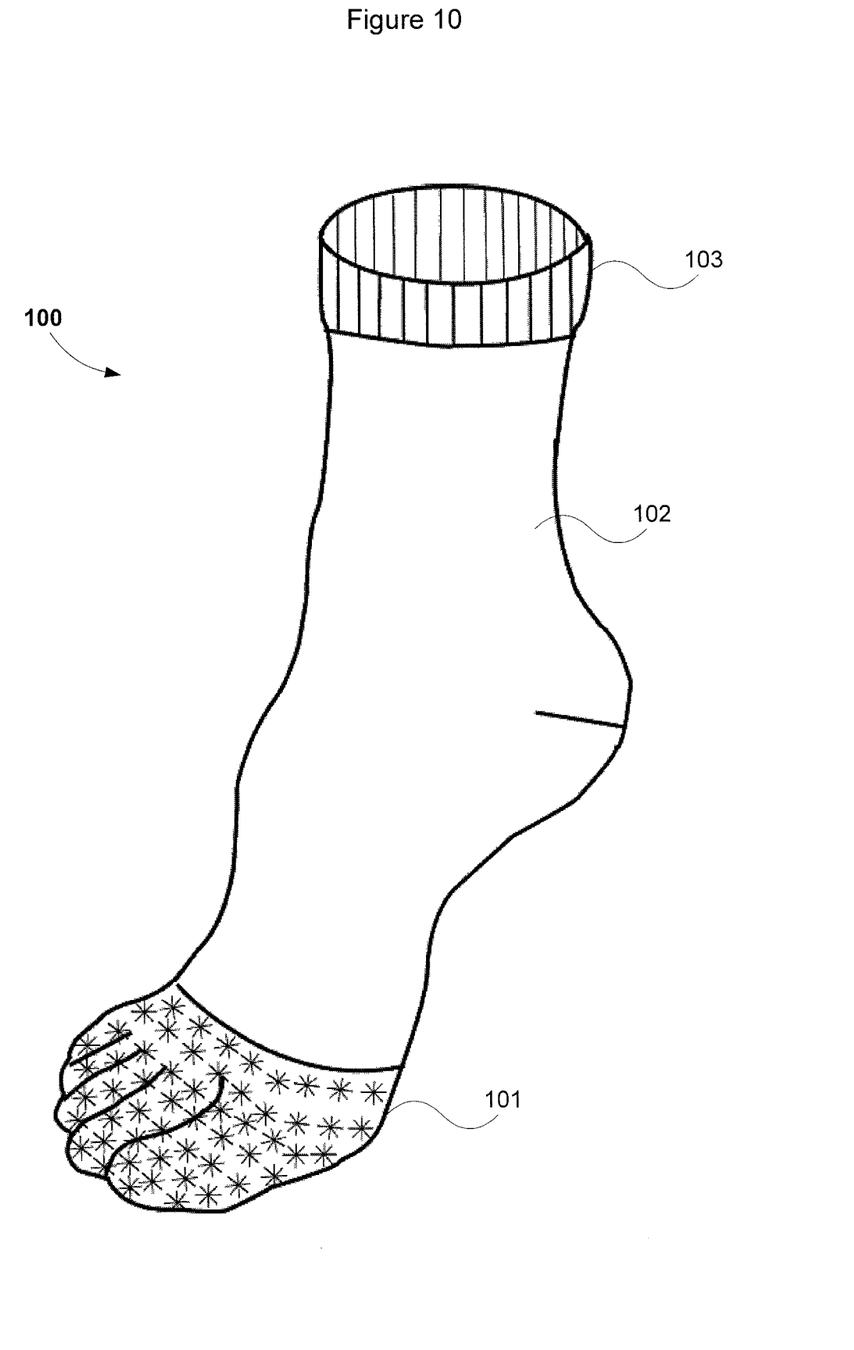
FIG. 10 is a schematic diagram of a sock for daily pharmacological treatment of a fungal infection in accordance with a second embodiment of the present invention.

Referring to FIG. 10, another sock design is depicted for a patient suffering from tinea pedis. The design of the sock 100 is suitable for patients suffering from interdigitial type tinea pedis as it separates each toe. This separation enables medicine and the antifungal agent to contact the skin between the toes. The textile material 20 at least in the toe area is moss stitched 101 and has a knitting structure in the form of a single jersey 102. There is a ribbed portion 103 on the upper opening of the sock 100 to hold the sock 100 tight up against the calf of the leg. The five toes design and the moss stitch structure increase the skin surface contact area in order to enhance the pharmacological treatment of patients with this type of tinea pedis.

Figure 11:
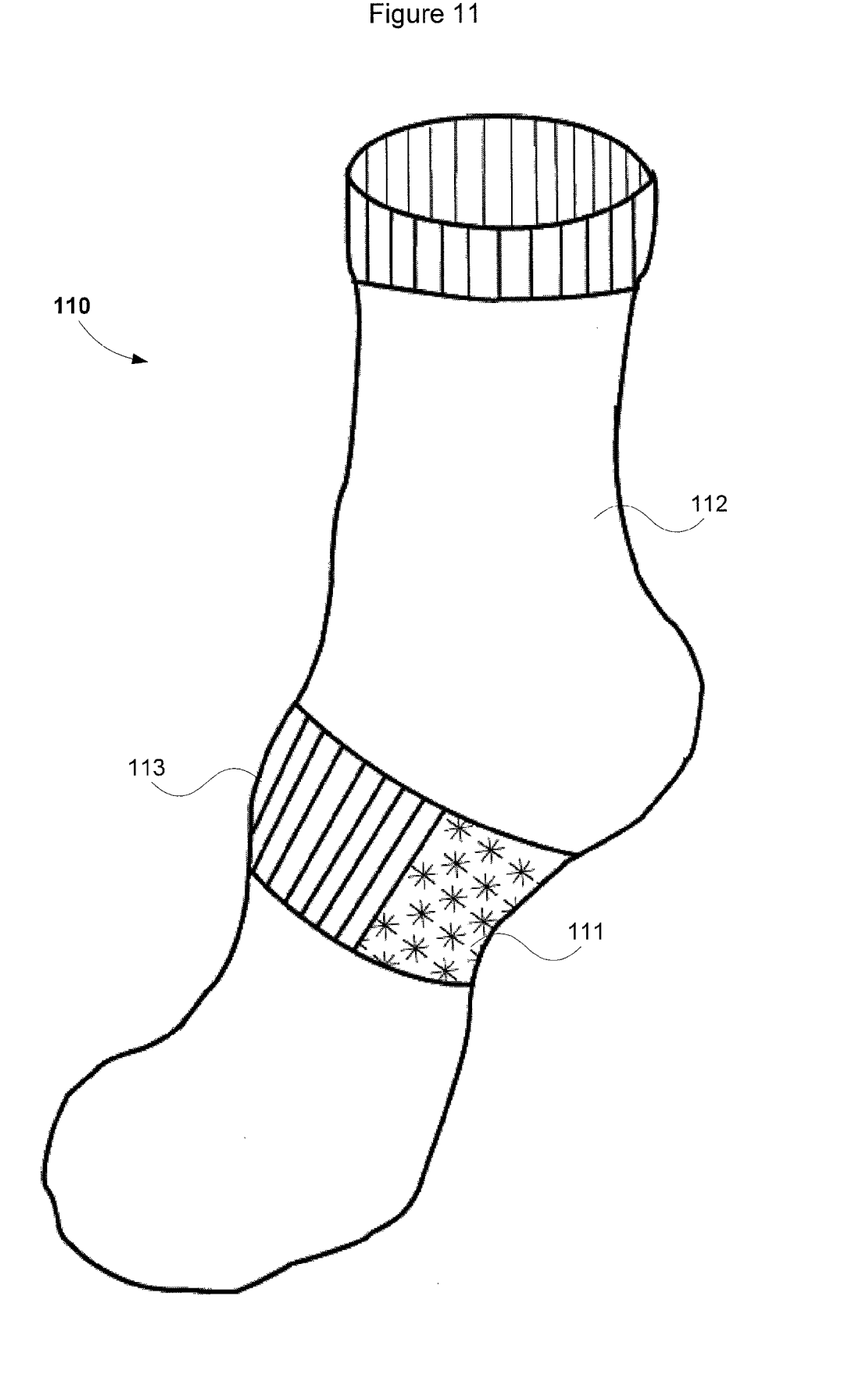
FIG. 11 is a schematic diagram of a sock for daily pharmacological treatment of a fungal infection in accordance with a third embodiment of the present invention.

Referring to FIG. 11, another sock design is depicted for a patient suffering from vesiculobullous type of tinea pedis. The sock 110 also has a knitting structure in the form of a single jersey 112. The ribbed portion 113 and moss stitch structure 111 are used in the middle of the thenar. This is because the ribbed portion 113 can provide a tighter fit while moss stitch 111 used at the instep and adjacent plantar surface can increase the contact area between infected part of foot with the medicine and antifungal agents.

Figure 12:
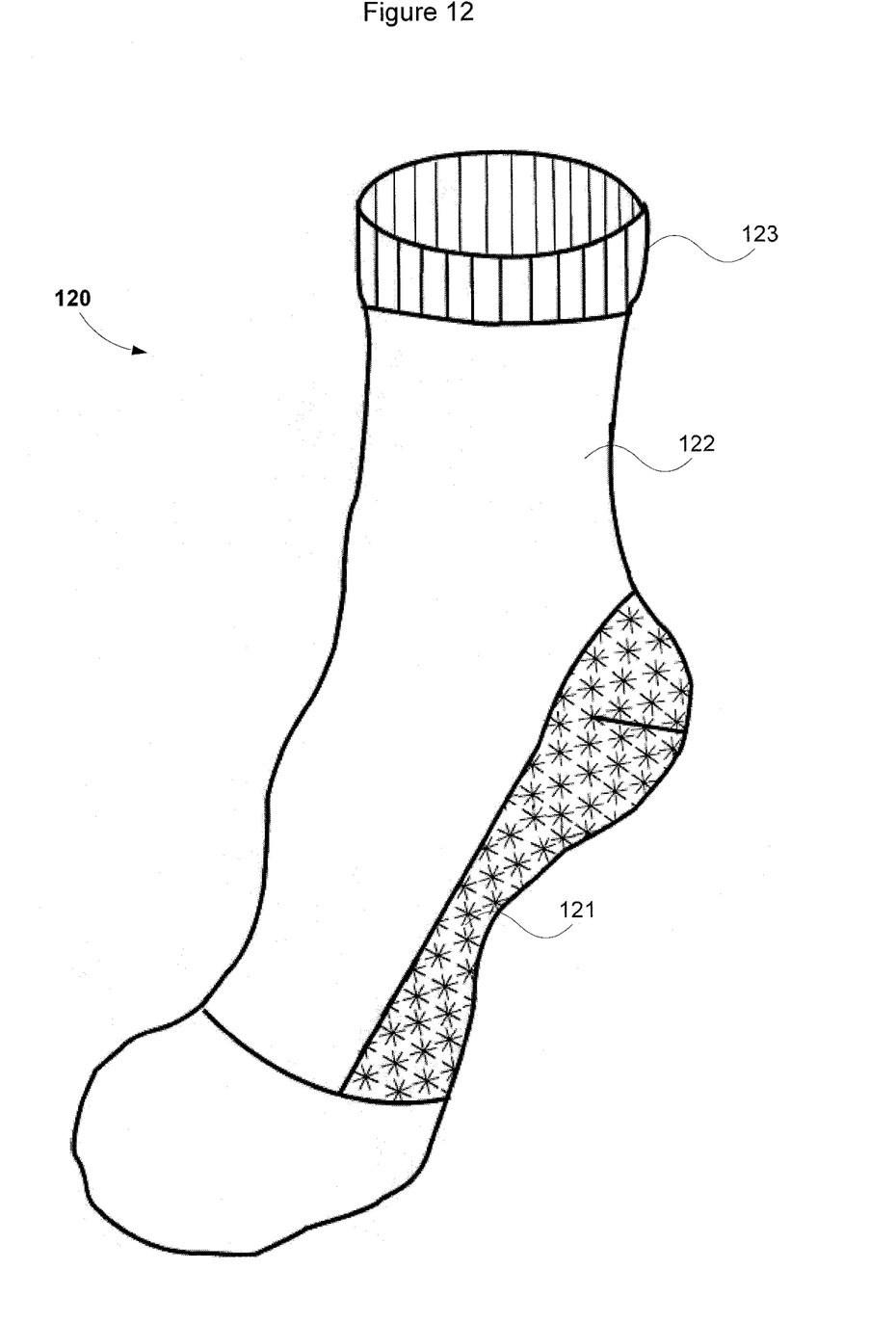
FIG. 12 is a schematic diagram of a sock for daily pharmacological treatment of a fungal infection in accordance with a fourth embodiment of the present invention.

Referring to FIG. 12, another sock design is depicted for a patient suffering from a bilateral moccasin type of tinea pedis. The sock 120 also has a knitting structure in the form of a single jersey 122. The moss stitch 121 is used at the soles and sides of the sock 120. There is a ribbed portion 123 on the upper opening of the sock 120 to hold the sock 120 tight up against the calf of the leg.

Figure 13:
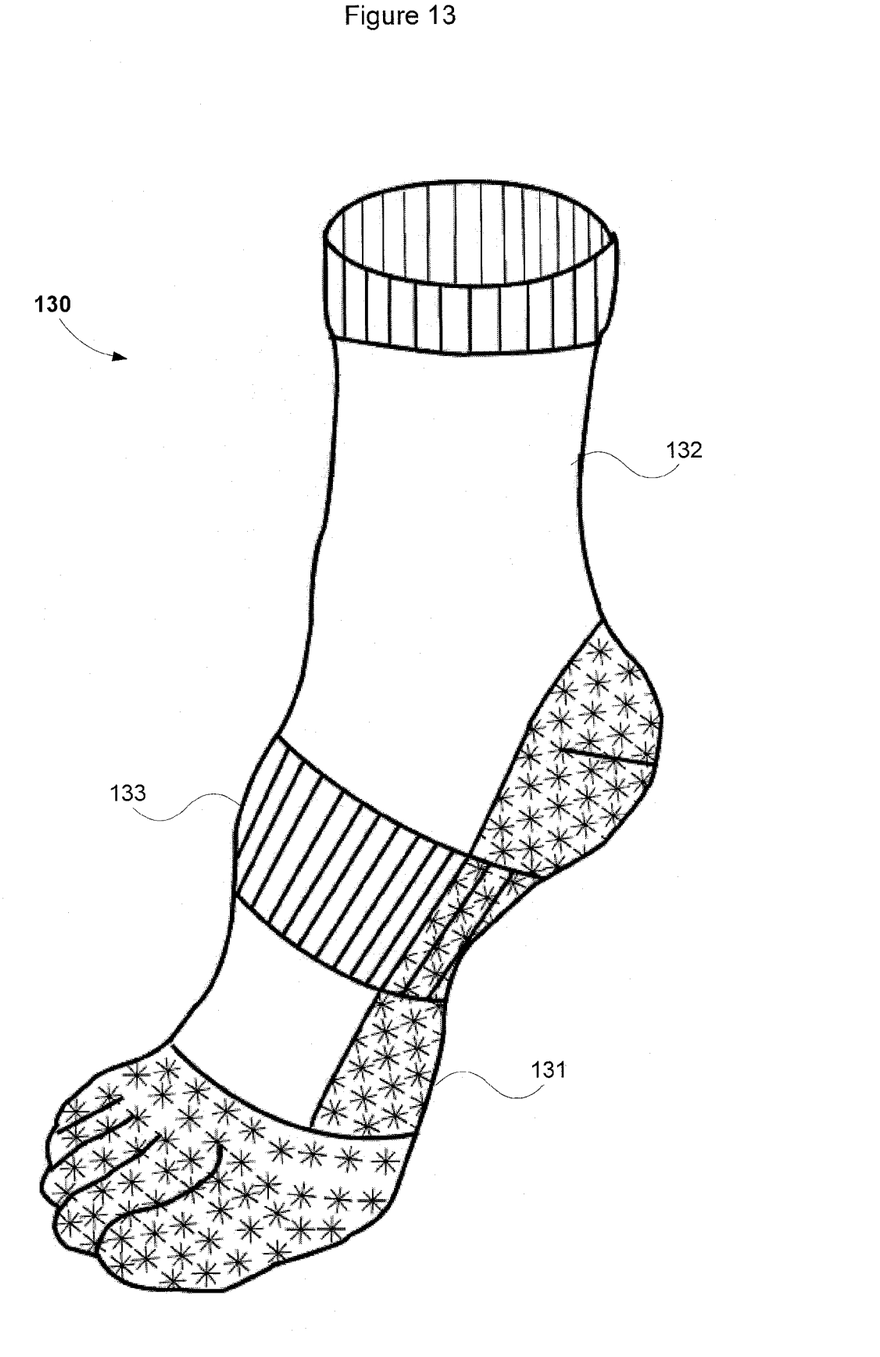
FIG. 13 is a schematic diagram of a sock for daily pharmacological treatment of a fungal infection in accordance with a fifth embodiment of the present invention.

Referring to FIG. 13, another sock design is depicted for a patient suffering from any type of tinea pedis with a combination of the previous sock designs. The sock 130 has a knitting structure also in the form of a single jersey 132. The moss stitch 131 is used at the toes, middle of the thenar, soles and sides of the sock 130. The ribbed portion 133 is used in the middle of the thenar. This is because the ribbed portion 133 can provide a tighter fit.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A sock for daily pharmacological treatment of a fungal infection, comprising:
   a tube-shaped body portion comprising a first open end and a second sealed end forming a toe portion, wherein the body portion comprises a textile material to manage moisture when the item of clothing is worn;
   microcapsules grafted on the textile material; and
   antifungal agents encapsulated within the microcapsules to pharmacologically treat the fungal infection when released from the microcapsules,
   wherein the tube-shaped body further comprises a moss stitched portion,
   wherein the moss stitched portion is disposed in the toe portion,
   wherein the antifungal agents are configured to be released from the microcapsules by friction between a user's skin and the textile material or by moisture from the skin, and wherein a wall shell for the microcapsules is formed of chitosan, and wherein the microcapsules are produced with the chitosan wall shell by coacervation.

2. The item of clothing according to claim 1, wherein the textile material is any one from the group consisting of: cotton, polyester, polyvinyl chloride (PVC), keratin fibers, wool, Spandex, Tencel, acrylic, bamboo fiber, flax, lyocell, rayon, and cellulosic acetates.

3. The item of clothing according to claim 1, wherein the fungal infection is any one from the group consisting of: interdigital tinea pedis, moccasin tinea pedis and vesiculobullous tinea pedis.

4. The item of clothing according to claim 1, wherein the sock is in the form of a toe sock and has at least one ribbed portion to tightly secure the sock to the foot.

5. The item of clothing according to claim 1, further comprising an anti-bacterial material contained in the textile material, the anti-bacterial material being any one from the group consisting of: ceramic magnetic powder, silver-ion, zinc-ion, potassium-ion copper-oxide, calcium-ion, titanium-dioxide, triclosan, chloroxylenol, chitosan and quaternary ammonium compounds.

6. The item of clothing according to claim 1, wherein the antifungal agents are released at a predetermined rate to ensure stability and control.

7. The item of clothing according to claim 1, wherein the antifungal agents are oil-soluble or water-soluble.

8. The item of clothing according to claim 7, wherein the oil-soluble agents include any one from the group consisting of: ketoconazole, clotrimazole, miconazole nitrate, sertaconazole nitrate, griseofulvin and tolnaftate.

9. The item of clothing according to claim 7, wherein the water-soluble agents include any one from the group consisting of: a salt form of amorolfine, ciclopirox butenafine, imidazole and terbinafine.

10. The item of clothing according to claim 1, wherein the item of clothing is to be worn only once for twelve hours for pharmacological treatment and as socks for further daily use.

11. The item of clothing according to claim 1, wherein the microcapsules are grafted on the textile material by any one from the group consisting of: padding, exhaustion, spraying and printing.

12. The item of clothing according to claim 1, wherein the microcapsules are grafted on the textile material by a surface modification method and thermal fixation.

13. The item of clothing according to claim 12, wherein the surface modification method is atmospheric pressure plasma (APP) treatment.

14. A system for pharmacological treatment of a disease or infection, the system comprising:
   an item of clothing made from a textile material, the item of clothing comprising a sock having a tube-shaped body portion comprising a first open end and a second sealed end forming a toe portion;
   microcapsules grafted on the textile material; and
   agents encapsulated within the microcapsules to pharmacologically treat the disease or infection when released from the microcapsules;
   wherein the microcapsules are grafted on the textile material by a surface modification method and thermal fixation,
   wherein the tube-shaped body further comprises a moss stitched portion,
   wherein the moss stitched portion is disposed in the toe portion,
   wherein the agents are configured to be released from the microcapsules by friction between a user's skin and the textile material or by moisture from the skin, and wherein a wall shell for the microcapsules is formed of chitosan, and wherein the microcapsules are produced with the chitosan wall shell by coacervation.

15. The system according to claim 14, wherein the surface modification method is atmospheric pressure plasma (APP) treatment.

16. The system according to claim 14, wherein the infection is a fungal infection which is any one from the group consisting of: interdigital tinea pedis, moccasin tinea pedis and vesiculobullous tinea pedis.

17. The system according to claim 14, wherein the textile material is any one from the group consisting of: cotton, polyester, polyvinyl chloride (PVC), keratin fibers, wool, Spandex, Tencel, acrylic, bamboo fiber, flax, lyocell, rayon, and cellulosic acetates.

18. A method comprising wearing the item of clothing of claim 1.

19. A sock for daily pharmacological treatment of a fungal infection, comprising:

a tube-shaped body portion comprising a first open end and a second sealed end forming a toe portion, wherein the body portion comprises a textile material;

microcapsules grafted on the textile material; and antifungal agents encapsulated within the microcapsules, wherein the tube-shaped body further comprises a moss stitched portion, wherein the moss stitched portion is disposed in the toe portion, and wherein the antifungal agents are configured to be released from the microcapsules by friction between a user's skin and the textile material or by moisture from the skin, and wherein a wall shell for the microcapsules is formed of chitosan, and wherein the microcapsules are produced with the chitosan wall shell by coacervation.

20. The sock according to claim 19, wherein the toe portion comprising a plurality of individual, separate toe pockets.

21. The sock according to claim 19, wherein the body portion further comprises a sole portion, and wherein the moss stitched portion is disposed in the sole portion.

22. The sock according to claim 19, wherein the body portion further comprises an instep portion, and wherein the moss stitched portion is disposed in the instep portion.

23. The sock according to claim 19, wherein the body portion further comprises an instep portion and a sole portion, and wherein the moss stitched portion is disposed in the instep portion, the sole portion and the toe portion.

24. A sock for daily pharmacological treatment of a fungal infection, comprising:

a tube-shaped body portion comprising a first open end and a second sealed end forming a toe portion, the body portion comprising a textile material, the toe portion comprising a plurality of individual, separate toe pockets;

microcapsules grafted on the textile material, the microcapsules being disposed in the toe portion around and between each of the individual, separate toe pockets; and antifungal agents encapsulated within the microcapsules, wherein the tube-shaped body further comprises a moss stitched portion, wherein the moss stitched portion is disposed in the toe portion, wherein the antifungal agents are configured to be released from the microcapsules by friction between a user's skin and the textile material or by moisture from the skin, and wherein a wall shell for the microcapsules is formed of chitosan, and wherein the microcapsules are produced with the chitosan wall shell by coacervation.

* * * * *